United States Patent [19]

Simon

[11] Patent Number: 5,374,562
[45] Date of Patent: Dec. 20, 1994

[54] PROCESS FOR THE DETERMINATION OF ALCOHOLS IN LIQUID OR GASEOUS SAMPLES

[75] Inventor: Wilhelm Simon, Zurich, Switzerland
[73] Assignee: Willi Moller AG, Zurich, Switzerland
[21] Appl. No.: 853,672
[22] Filed: Mar. 19, 1992
[30] Foreign Application Priority Data Mar. 21, 1991 [CH] Switzerland .................. 875/91

[51] Int. Cl.$^5$ ........................... G01N 33/14
[52] U.S. Cl. .................. 436/131; 436/127; 436/132; 436/169; 436/172; 436/178; 422/84; 422/85; 422/86; 422/87
[58] Field of Search .............. 422/82.05–82.09, 422/84–87; 436/68, 127, 131, 132, 169, 172, 178, 900; 534/770, 795, 851; 568/331, 335, 592

[56] References Cited

U.S. PATENT DOCUMENTS

| | | | |
|---|---|---|---|
| 1,689,901 | 10/1928 | Williams | 436/178 X |
| 2,217,693 | 10/1940 | McNally et al. | 534/851 X |
| 2,226,199 | 12/1940 | Dickey | 534/851 X |
| 2,855,439 | 10/1958 | Kundiger et al. | 568/335 |
| 3,150,187 | 9/1964 | Cavallini et al. | 568/331 X |
| 3,184,379 | 5/1965 | Lukes et al. | 568/335 X |
| 3,251,733 | 5/1966 | Bindler et al. | 568/331 X |
| 3,330,872 | 7/1967 | Weesner | 568/335 X |
| 3,524,889 | 8/1970 | Sims | 568/592 |
| 3,647,879 | 3/1972 | Massarani et al. | 568/335 X |
| 3,714,168 | 1/1973 | Olsen | 568/331 X |
| 3,911,016 | 10/1975 | Klingder et al. | 568/335 X |
| 4,272,485 | 6/1981 | Lübbers | 422/82.05 X |
| 4,358,308 | 11/1982 | Swithenbank | 568/331 X |
| 4,587,101 | 5/1986 | Marsoner et al. | 436/172 X |
| 4,724,267 | 2/1988 | St. George et al. | 568/331 X |
| 5,004,832 | 4/1991 | Castaldi et al. | 568/592 X |
| 5,037,968 | 8/1991 | Simon et al. | 436/172 X |
| 5,142,092 | 8/1992 | Kysela et al. | 568/335 X |

FOREIGN PATENT DOCUMENTS 0281829 9/1988 European Pat. Off. .

OTHER PUBLICATIONS

C. Behringer et al., Analytica Chimica Acta, 233, 1990, Elsevier Science publishers B.V., pp. 41–47.
F. L. Dickert et al., Analytical Chemistry, 60 No. 14, 15, Jul. 1988, American Chemical Society, pp. 1377–1380.
R. Stewart et al. Can. J. Chem. 1980, 58, 2491–2496.
L. S. Chen et al. J. Fluorine Chem. 1981, 18, 117–129.
P. J. Wagner et al. J. Am. Chem. Soc. 1986, 108, 7739–7744.
M. Uieara et al J. Chem. Soc., Perkin Trans 2 1987, 175–179.
R. Stewart et al. Can. J. Chem. 1970, 48, 3961–3962.
J. P. Guthrie Can. J. Chem. 1974, 53, 898–906.
M. E. Meyerhoff et al. Anal. Chem., 1987, 59, 144–150.
K. Seiler et al. Anal. Chim. Acta 1991, 244, 151–160.
L. Toke et al. Acta Chim. Hung. 1986, 122, 103–109.

Primary Examiner—James C. Housel
Assistant Examiner—Arlen Soderquist
Attorney, Agent, or Firm—Seidel, Gonda, Lavorgna & Monaco

[57] ABSTRACT

Hemiacetals are disclosed which correspond to the following formula II

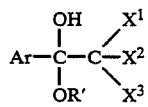

in which

R' is an aliphatic or cycloaliphatic residue,

Ar is an unsubstituted or substituted monocyclic or polycyclic aromatic or heteroaromatic residue and $X^1$, $X^2$ and $X^3$ are selected from the group consisting of hydrogen, alkyl, alkenyl, alkynyl, fluoro, chloro, bromo and nitro, wherein however at least one of said substituents has to be selected from the stated halo atoms or nitro. The hemiacetals are formed reversibly from an alcohol and a corresponding keto compound and the hemiacetals of formula II differ from the corresponding keto compounds as to their light absorption in the ultraviolet, visible or infrared range, or a fluorescence or luminescence is created or quenched when the keto compound is converted into the hemiacetal of formula II. Said reaction can be performed in sensors which are used for the optical determination of alcohols.

21 Claims, No Drawings

PROCESS FOR THE DETERMINATION OF ALCOHOLS IN LIQUID OR GASEOUS SAMPLES

BACKGROUND OF THE INVENTION

The present invention concerns new hemiacetals which are formed reversibly if keto compounds are contacted with an aliphatic or cycloaliphatic alcohol. The corresponding hemiacetals differ from the keto compounds from which they are formed with regard to their light absorption in the ultraviolet, in the visible or in the infrared range of wave length, or when the hemiacetal is formed from the keto compound through a reversible reaction with said aliphatic or cycloaliphatic alcohol a luminescence or fluorescence is created or quenched.

The present invention furthermore concerns an optical sensor for the determination of aliphatic or cycloaliphatic alcohols in liquid or gaseous samples, which sensor contains a keto compound which is converted into the new hemiacetal if said sensor is contacted with a corresponding sample which contains said aliphatic or cycloaliphatic alcohol. Through the contact of the the sensor with an alcohol containing sample, its light absorption in the ultraviolet, visible or infrared range of wave length, is changed or a fluorescence or a luminescence is induced or quenched.

DESCRIPTION OF THE PRIOR ART

A fast determination of alcohols, preferably of ethanol in biologic material, is desirable, and such a determination is important if in alcoholic beverages the alcohol content has to be tested, and the determination of ethanol and other alcohols during the performance of biotechnological processes is as well important. With regard to this there is referred to the publications of A. Wieseman, Trends Anal. Chem. 7 (1988) 5 and of J. Ruz, A. Fernandes M.D., Luquede Castro and M.J. Yalcacel, Pharm. Biomed. Anal., 4 (1986) 559.

If ethanol has to be determined it is usually converted enzymatically. If said enzymatic conversion is performed with an alcohol-oxydase, then the concentration of ethanol can be determined quantitatively or semiquantitatively by measuring the consumption of oxygen during said enzymatic reaction. With regard to this we e.g. refer to the publication of K. P. Völkl, N. Opitz and W. D. Löbbers, Fresenius Z., Anal. Chem., 301 (1980) 162 as well as to the publication of O.S. Wolfbeis and H. E. Posch, Fresenius Z., Anal. Chem., 332 (1988) 255.

It however is also possible to perform the enzymatic conversion of ethanol using dehydrogenase. In this case the concentration of said alcohol is usually determined by monitoring optically the velocity of the formation of side-products. For example the velocity of the conversion of the nicotinamide-adenine-dinucleotide, which is abbreviated as NAD, from its oxidized form into its reduced form, which is abbreviated as NADH, can be observed. In many publications such enzymatic methods for the determination of ethanol are described, and as example of such publications there is referred to the recently printed publication of S. M. Gautier, L. J. Blum and P. R. Coulet in J. Biolumin. Chemilumin., 5 (1990) 57.

Analytical processes which are based on enzymatic reactions, however, usually have the disadvantage that their performance is rather complicated and time-consuming, and furthermore they are accompanied with the risk of false test results due to a decomposition of the enzyme component during the storage or due to a poisoning of the enzyme component.

It is furthermore well known in the art that dye-stuffs based on triphenylmethane alter their optical properties if they are contacted with vapors of polar solvents, including alcohol vapors. Such dye-stuffs were already used for performing corresponding analyses in a continuous way. With regard to this we refer to the publication of H. E. Posch, O. S. Wolfbeis and J. Pusterhofer, Talanta, 35 (1988) 89. Furthermore in the publication of F. L. Diekert, E. H. Lehmann, S. K. Schreiner, H. Kimmel and G. R. Mages, Anal. Chem. 60 (1988), pages 1377–1388, there are described corresponding sensors for vapors of polar solvents in which the dye-stuff is a lactone of a triphenyl substituted methanol in which to each of the three phenyl groups of the triphenyl methane moiety there is bonded in the p-position thereof a dimethylamino group. One of said phenyl groups is furthermore substituted with a carboxylic acid group in the o-position thereof, which forms together with the hydroxy group of the corresponding methanol derivative the five-membered lactone ring. The lactone ring however is cleaved forming the colored triphenyl carbenium ions which have a characteristic absorption band at 610 nm. The corresponding dye-stuffs can be used as chemical sensors for ethanol or other polar solvents.

An essential disadvantage of the sensors which are described in said publication, is that the corresponding test results are falsified through the humidity of the environment (see specially FIG. 4 on page 1379, left column, of said publication) and that furthermore the sensor is not at all selective for alcohols, but also polar solvents like acetone and ethylacetate give a corresponding response (see FIG. 7 on page 1379, right column).

Commonly used are furthermore apparatus for a semiquantitative determination of the ethanol level of the blood of tested persons via the air which is exhaled by said person. The corresponding apparatuses are available on the market with the Trademark "Alcotest". The corresponding apparatus contain chromosulfuric acid (mixture of an alkalidichromate with sulfuric acid which is colored yellow) on an inert carrier material, and if said product is brought into contact with ethanol, the color changes to green due to a reduction of the chromosulphuric acid to chromo(III) compounds. Said color reaction of course is not selective for alcohols, but the changing of the color to green is also to be observed if the equipment comes into contact with any substance which is oxidized under the stated conditions through chromosulfuric acid.

In the European patent publication no. 0 281 829 (publication day Sep. 14, 1988) of Willi Möller AG, and in the corresponding U.S. Pat. No. 5 037 968 of Simon et al., there are described keto compounds which interact with anions of oxaacids and are able to form an adduct with said oxaacids. As examples of anions of oxa-acids which form adducts with said keto compounds, there are mentioned in said publications the anions of carboxylic acids, hydroxy carboxylic acids, keto carboxylic acids, amino carboxylic acids, as well as the anions of peptides and furthermore the anions of inorganic oxaacids, like carbonate anions, bicarbonate anions and phosphate anions. The corresponding keto compounds have a $\pi$-electron system, which is conjugated with the keto group, and furthermore a strongly electron attracting substituent in their structure. Preferred such keto compounds which have the ability of forming adducts with the anions of oxaacids are monoketons which correspond to the following formula A

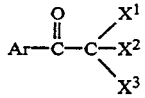   A in which
Ar is an aromatic or heteroaromatic residue and $X^1$, $X^2$ and $X^3$ are independently from each other hydrogen atoms, alkyl groups, alkenyl groups, alkynyl groups, fluoro atoms, chloro atoms, bromo atoms or nitro groups, with the provision that however at least one of said substituents is a strongly electron attracting substituent, selected from the group comprising fluoro atoms, chloro atoms, bromo atoms and nitro groups.

Corresponding keto compounds of formula A in which
Ar is a phenyl nucleus which is substituted in the p-position to the keto group with a substituent which is selected from dialkyl amino groups, acylated monoalkyl amino groups, carboxylic acid ester groups, carboxylic acid amide groups, alkyl groups, ether groups, thioether groups and sulfoxide groups, and in which furthermore
$X^1$, $X^2$ and $X^3$ is a fluoro atom are described in the publication of Christoph Behringer, Beatrice Lehmann, Jean-Pierre Haug, Kurt Seiler, Werner E. Morf, Karel Hartman and Wilhelm Simon in Analytica Chimica Acta, volume 233, 1990, pages 41–47. In said publication the selectivity of the corresponding trifluoro-methyl ketone for carbonate anions over chloride anions was determined and also the hydratation of said compounds through humidity was investigated.

It was the aim of the present invention to develop new sensors which react more specifically with aliphatic and cycloaliphatic alcohols than the triphenylmethane dyes described in the prior art, and which sensors form with said alcohols reaction products which differ from the starting materials from which they were formed through the light absorption in the ultraviolet, the visible or infrared range of wave length, or wherein in the course of the reaction with said alcohol, a fluorescence or a luminescence is created or quenched. It furthermore was the aim of the present invention to provide a new system for an optical determination of alcohols which does not have the disadvantages of the prior art systems which are based on enzymatic reactions.

In the course of said search, new hemiacetals were found which are the reaction product of alcohols with keto compounds which are either new keto compounds or keto compounds which are already described in the prior art, including such which correspond to the above stated formula A.

It was surprisingly found out that the corresponding hemiacetals are formed reversibly from the keto compounds used as starting materials and that furthermore the hemiacetals differ from said keto compounds as to their light absorption in the ultraviolet, the visible or the infrared range of wave length, or that in the course of the formation of the hemiacetal from the keto compound used as starting materials, a fluorescence or a luminescence is developed or quenched.

DESCRIPTION OF THE INVENTION

One object of the present invention is a hemiacetal which is formed reversibly from an alcohol and a keto compound, and said hemiacetal is a new compound which corresponds to the following formula II

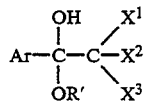   II in which
R' is an aliphatic or cycloaliphatic residue,
Ar is an unsubstituted or substituted monocyclic or polycyclic, aromatic residue or an unsubstituted or substituted monocyclic or polycyclic heteroaromatic residue in which residue the substituents are nonpolar substituents, substituents having only weakly polar properties, substituents having basic properties and/or chromophorous substituents, respectively groups which induce a fluorescence or a luminescence and
$X^1$, $X^2$ and $X^3$ are independently from each other selected from the group consisting of hydrogen atoms, alkyl groups, alkenyl groups, alkynyl groups, fluoro atoms, chloro atoms, bromo atoms and nitro groups, provided that however at least one of the substituents $X^1$, $X^2$ and $X^3$ is a strongly electron attacting substituent, selected from the group consisting of fluoro atoms, chloro atoms, bromo atoms and nitro groups, and
wherein the hemiacetal having the formula II differs from the keto compound of formula I

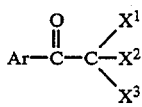   I from which it was formed with regard to its light absorption in the ultraviolet, in the visible or in the infrared range of wave length or wherein when the hemiacetal of formula II is formed from the keto compound of formula I and the alcohol of formula

a fluorescence or a luminescence is created or quenched.

In preferred new hemiacetals which correspond to formula II
Ar is selected from the following aromatic or heteroaromatic ring systems:
(a) aromatic systems selected from the groups consisting of unsubstituted or substituted benzene, unsubstituted or substituted naphthalene, unsubstituted or substituted phenantrene or unsubstituted or substituted anthracene, in which systems the substituents are selected from the group of substituents which are defined above for the generic formula II and (b) unsubstituted or substituted monocyclic or polycyclic heterocyclic systems selected from the group consisting of unsubstituted or substituted thiophene, unsubstituted or substituted furan, unsubstituted or substituted benzofuran, unsubstituted or substituted benzothiophene and monocyclic or polycyclic heteroaromatic residues which comprise in their structure at least one heteroatom which is nitrogen and which nitrogen containing heteroaromatic residues are selected from the group consisting of unsubstituted or substituted pyrrole, unsubstituted or substituted 1,2 or 1,3-diazole, unsubstituted or substituted triazole, unsubstituted or substituted pyridine, unsubstituted or substituted thiazole, unsubstituted or substituted 1,2-diazine, unsubstituted or substituted 1,3-diazine, unsubstituted or substituted 1,4-diazine (pyrazine), unsubstituted or substituted 1,3,5-triazine, unsubstituted or substituted 1,2,4-triazine, unsubstituted or substituted 1,2,3-triazine, unsubstituted or substituted tetrazine, unsubstituted or substituted 1-azanaphthalene (quinoline), unsubstituted or substituted 2-azanaphthalene (isoquinoline), unsubstituted or substituted diazanaphthalenes, unsubstituted or substituted triazanaphthalenes, unsubstituted or substituted indole, unsubstituted or substituted carbazole, unsubstituted or substituted monoazaantracenes, like acridine, unsubstituted or substituted monoazaphenantrenes, like phenathridine, unsubstituted or substituted diaazaanthracenes, unsubstituted or substituted diazaphenthrenes, like phenanthrolines, unsubstituted or substituted triazaanthracenes, unsubstituted or substituted triazaphenanthrenes, unsubstituted or substituted tetraazaanthracenes and unsubstituted or substituted tetraazaphenanthrenes, and wherein in said substituted aromatic systems and heterocyclic systems the substituents are selected from the group of substituents defined in claim 1.

In the hemiacetals of formula II and in the preferred hemiacetals of formula II in which Ar is an aromatic system as defined above in passage (a) or a heteroaromatic system as defined above in passage (b), there are bonded to the corresponding aromatic or heteroaromatic systems 0–5 substituents, preferably 1–4 substituents which are nonpolar substituents or substituents having only weakly polar properties, or substituents having basic properties and/or chromophorous substituents, respectively groups which induce a fluorescence or luminescence.

Preferred examples of corresponding substituents which have nonpolar properties or only slightly polar properties are selected from the group halo atoms, nitro groups, unsubstituted or substituted alkyl groups, unsubstituted or substituted alkenyl groups comprising one or more carbon-carbon-double bonds, unsubstituted or substituted alkynyl groups, unsubstituted or substituted cycloalkyl groups, unsubstituted or substituted aryl groups, unsubstituted or substituted heterocyclic residues, and wherein the substituents which are present in the above stated substituted groups are unpolar substituents or substituents having slightly polar properties or substituents having basic properties or wherein the substituents which are bonded to the aromatic or heteroaromatic residue Ar are ether groups, groups of formula —S—R$^1$, —SO—R$^1$ or —SO$_2$—R$^1$, nitrilo groups, carboxylic acid ester groups, carboxylic acid amide or sulfonic acid amide groups, hydroxy groups or esterified hydroxy groups.

In the above sulfur containing groups of the stated formula, R$^1$ is hydrogen or preferably an unsubstituted or substituted alkyl radical, an unsubstituted or substituted alkenyl radical, an unsubstituted or substituted cycloalkyl radical, an unsubstituted or substituted aryl radical or an unsubstituted or substituted heterocycle.

Preferred examples for substituents having basic properties which are bonded to the aromatic or heteroaromatic ring system Ar of the hemiacetals of formula II, respectively to the preferred aromatic systems defined above with (a) and the preferred heteroaromatic systems defined above in (b), are primary or secondary or tertiary amino groups or acylated amino groups which groups correspond to the following formula

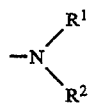

wherein the radicals R$^1$ and R$^2$ are independently from each other selected from the groups consisting of hydrogen atoms, unsubstituted or substituted alkyl residues, unsubstituted or substituted alkenyl residues, unsubstituted or substituted alkynyl residues, unsubstituted or substituted cycloalkyl radicals, unsubstituted or substituted aryl radicals, unsubstituted or substituted heterocyclic radicals, and acyl groups which correspond to the formula

or to the formula

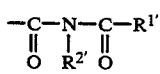

in which acyl groups the radicals
R$^{1'}$ and R$^{2'}$ are independently from each other selected from the groups consisting of hydrogen atoms, unsubstituted or substituted alkyl residues, unsubstituted or substituted alkenyl residues, unsubsituted or substituted alkynyl residues, unsubstituted or substituted cycloalkyl radicals, unsubstituted or substituted aryl radicals and unsubsituted or substituted heter cyclic radicals or
R$^1$ and R$^2$ form together with the nitrogen atom to which they are bonded, a heterocyclic residue which can have in its ring structure no further hetero atoms or further hetero atoms which are selected from the group consisting of oxygen, sulfur or nitrogen, and which heterocyclic radical is unsubstituted or substituted with substituents which are nonpolar substituents or substituents having only weakly polar properties.

In as far as the substituents which are bonded to the aromatic or heteroaromatic structure Ar of the hemiacetals of formula II are concerned said substituents can be also any desired combinations of the substituents outlined above, and accordingly the corresponding substituents bonded to the aromatic or heteroaromatic structure and also the substituents R$^1$ defined above with regard to the sulfur containing compounds, respectively the substituents $R^1$, $R^2$ and $R^{1'}$ as well as $R^{2'}$ defined with regard to the substituents having basic properties, can e.g. be aryl substituted alkyl groups, alkyl or aryl groups which are bonded via ether groups and which are substituted with primary, secondary or tertiary amino groups or acyl amino groups, for example the corresponding groups defined above with regard to the substituents having basic properties.

In a preferred class of the new hemiacetals of formula II, respectively in preferred keto compounds of formula I which are used as starting materials for the preparation of said hemiacetals, there are furthermore bonded to the aromatic or heteroaromatic residue Ar, preferably to an aromatic residue as defined in (a) above, or a heteroaromatic residue as defined in (b), chromophorous groups, respectively groups which induce a fluorescence or luminescence. Preferably said groups are selected from azo groups or azo groups to which there are bonded aromatic or heteroaromatic residues or systems which have two or more conjugated double bonds or conjugated triple bonds.

A preferred example for a new hemiacetal of formula II which comprises such a chromophoric group which is bonded to the aromatic or heteroaromatic residue, is the azo hemiacetal of formula IV

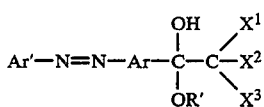

in which

Ar and Ar' are independently from each other unsubstituted or substituted monocyclic or polycyclic, aromatic residues or unsubstituted or substituted monocyclic or polycyclic heteroaromatic residues in which residues the substituents are nonpolar substituents, substituents having only weakly polar properties, substituents having basic properties and $X^1$, $X^2$ and $X^3$ are independently from each other selected from the group consisting of hydrogen atoms, alkyl groups, alkenyl groups, alkynyl groups, fluoro atoms, chloro atoms, bromo atoms and nitro groups, provided that however at least one of the substituents $X^1$, $X^2$ and $X^3$ is a strongly electron attracting substituent, selected from the group consisting of fluoro atoms, chloro atoms, bromo atoms and nitro groups.

In said hemiacetals of formula IV the residue Ar as well as the residue Ar' is preferably selected from the aromatic residues defined above in passage (a), and the corresponding heteroaromatic residues are preferably selected from the groups of heterocycles defined in passage (b) above.

In the azo hemiacetals of formula IV, accordingly both radicals Ar and Ar' can be monocyclic or polycyclic aromatic residues which have an identical or a different structure or both of the radicals Ar and Ar' can be monocyclic or polycyclic heteroaromatic radicals of the same or a different structure.

It however was unexpectedly found out that specially advantageous properties as to an alternation of the optical properties are achieved if in the new azo hemoacetals of the above stated formula IV, one of the radicals Ar and Ar' is a monocyclic or polycyclic aromatic residue, and the other of said two residues is a monocyclic or polynuclear heteroaromatic residue. Of said preferred group of hemiacetals of formula IV those are specially preferred in which Ar is an aromatic residue, preferably a benzene nucleus, and the radical Ar' is a heteroaromatic residue.

The azo hemiacetals of formula IV are reversibly formed if an azo keto compound of formula III

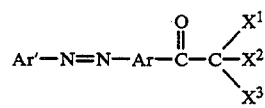

is brought into contact with an alcohol of formula

R'—OH.

There can be clearly seen that in the azo keto compound of formula III the double bond of the keto group is conjugated to the aromatic or heteroaromatic nucleus Ar, and it furthermore can be also conjugated via said aromatic or heteroaromatic group to the azo group and to the further aromatic or heteroaromatic radical Ar'. When said azo keto compound of formula III is converted into the hemiacetal of formula IV through the reaction with said alcohol, then the CO double bond of the carbonyl group is removed from the molecular structure, and accordingly also the conjugation of said group with the corresponding aromatic or heteroaromatic residue Ar. This results in that the absorption is shifted to a range of shorter wave length (hypsochromic shifting) if the keto compound of formula III is converted to the corresponding hemiacetal of formula IV. Accordingly, if the keto compound of formula III has an absorption in the visible range of wave length, then the corresponding compound alters its color if the keto compound of formula III is converted to the hemiacetal of formula IV or the color of the keto compound of formula III disappears if the corresponding hemiacetal of formula IV has an absorption in the ultraviolet region of wave length.

It is clearly evident that in those keto compounds of formula III in which the radical Ar is a benzene nucleus, the optimal conjugation of the carbonyl group with said benzene nucleus and with the azo group and the further aromatic or heteroaromatic residue Ar' is given if the azo group is bonded to the residue Ar in para-position to the carbonyl group. Said position therefore is preferred because in this case the shifting of the light absorption is improved when the keto compound of formula III is converted into the hemiacetal of formula IV. Analogous considerations as to the position of the azo group are also true if the group Ar is an aromatic structure having further condensed aromatic nuclei or a heteroaromatic structure. Tests have shown that the shifting of the light absorption is specially high if in the keto azo compounds of formula III the radical Ar is an aromatic radical, preferably one in which the azo group is bonded in the para-position to the keto group, and in which furthermore the residue Ar' is a heterocyclic radical which contains nitrogen or sulfur, and specially preferred nitrogen and furthermore also sulfur. Therefore, a preferred heteroaromatic radical Ar' is a thiazol.

A preferred azo hemiacetal of formula IV is accordingly the hemiacetal which has the following structure

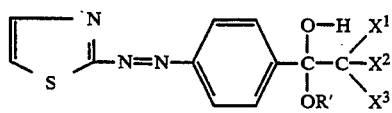

In said thiazole derivatives there are optionally present in the benzene nucleus and optionally furthermore also in the thiazole nucleus further substituents, preferably such substituents which are mentioned before as preferred substituents of the aromatic or heteroaromatic residues Ar.

It is essential for the inventive hemiacetals of formula II that at least one of the groups $X^1$, $X^2$ and $X^3$ is a strongly electron attracting substituent which is selected from the group comprising fluoro atoms, chloro atoms, bromo atoms or nitro groups. Only if such a substituent is present on the carbon atom in the neighbour position to the carbonyl group of the corresponding keto compounds of formula I, a fast and reversible conversion of said keto compounds of formula I into the hemiacetal is achieved if said keto compound of formula I comes into contact with a corresponding alcohol.

In preferred hemiacetals of formula II and also in preferred hemiacetals of formula IV, at least two of the substituents $X^1$, $X^2$ and $X^3$ are selected from the group consisting of fluoro atoms, chloro atoms, bromo atoms and nitro groups, and in specially preferred compounds having said formula, all of the residues $X^1$, $X^2$ and $X^3$ are fluoro atoms and/or chloro atoms.

Specially preferred are those hemiacetals of formula II and formula III respectively, in which the group having the formula

is the trifluoro methyl group.

In the new hemiacetals of formula II, in the preferred hemiacetals wherein Ar is one of the stated preferred monocyclic or polycyclic aromatic or heteroaromatic residues and wherein the corresponding substituents, if present, have the preferred meanings outlined before, as well as also in the azo hemiacetals of formula IV, R′ is an aliphatic or cycloaliphatic residue. Preferably the residue R′ is an alkyl group having 1–10 carbon atoms, and specially preferred said radical R′ is derived from a primary alcohol comprising 1–10 carbon atoms.

Specially preferred are such hemiacetals in which R′ is an alkyl group comprising 1–5 carbon atoms, and still more preferred alkyl groups, are derived from primary alkanols of formula

wherein $R^3$ is hydrogen or an alkyl group having 1–4 carbon atoms.

A further object of the present invention is a process for the preparation of the new inventive hemiacetals of formula II

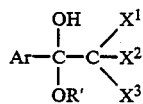

in which
R′, Ar, $X^1$, $X^2$ and $X^3$ are as defined before, wherein a keto compound having the formula I

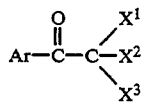

is reacted with an alcohol of formula

R′OH to form said hemiacetal of formula II.

According to a preferred embodiment of the process for performing the preparation of the inventive hemiacetals of formula II the keto compound of formula I is a component of an optical sensor and according to said embodiment the alcohol of formula

R′OH is brought into contact with said sensor, and thereby the keto compound of formula I is converted into the corresponding hemiacetal of formula II through the reversible reaction with said alcohol, and through said conversion of the keto compound of formula I into the hemiacetal of formula II, the light absorption of said optical sensor is changed in the ultraviolet, the visible and the infrared range of wave length, or wherein through the conversion of the keto compound of formula I into the hemiacetal of formula II, a fluorescence or a luminescence is created or quenched.

According to said preferred performance of the inventive process for the preparation of the hemiacetal of formula II said process is used in order to make possible a determination of aliphatic alcohols or cycloaliphatic alcohols by optical means, which determination is easily to be performed, and a corresponding alcohol can be determined in samples qualitatively or quantitatively.

A further object of the present invention accordingly is an optical sensor for the determination of alcohols of formula

R′—OH in which
R′ is an aliphatic or cycloaliphatic residue, in liquid or gaseous samples, which sensor contains a keto compound of formula I

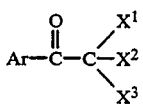

in which
Ar is an unsubstituted or substituted monocyclic or polynuclear, aromatic residue or an unsubstituted or substituted monocyclic or polycyclic heteroaromatic residue in which residue the substituents are nonpolar substituents, substituents having only weakly polar properties, substituents having basic properties and/or chromophorous substituents, respectively groups which induce a fluorescence or a luminescence and $X^1$, $X^2$ and $X^3$ are independently from each other selected from the group consisting of hydrogen atoms, alkyl groups, alkenyl groups, alkynyl groups, fluoro atoms, chloro atoms, bromo atoms and nitro groups, provided that however at least one of the substituents $X^1$, $X^2$ and $X^3$ is a strongly electron attracting substituent, selected from the group consisting of fluoro atoms, chloro atoms, bromo atoms and nitro groups, and wherein said keto compound of formula I is converted into a hemiacetal of formula II

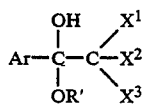

if in the liquid or gaseous sample there is present the alcohol of the stated formula and wherein the keto compound of formula I differs from the hemiacetal of formula II with regard to its light absorption in the ultraviolet, in the visible or in the infrared range of wave length or wherein through the conversion of the keto compound of formula I into the hemiacetal of formula II a fluorescence or a luminescence is created or quenched.

Preferably said optical sensor contains keto compounds of formula I in which Ar is an aromatic or heteroaromatic ring system as defined in passage (a) or an unsubstituted or substituted monocyclic or polycyclic heterocyclic ring system selected from the group which is defined before in passage (b).

Preferred substituents in the corresponding substituted aromatic or heteroaromatic ring systems are those which were defined before, and furthermore preferred keto compounds of formula I which are used in said sensor are the azo keto compounds which have the formula III stated before, like for instance the azo keto compounds which upon contact with the alcohol to be determined, yield the corresponding hemiacetals which have in their structure a thiazole residue and a benzene nucleus bonded to the azo group, the formula of which is stated before.

The inventive sensors are used to determine qualitatively or quantitatively aliphatic or cycloaliphatic alcohols of formula

in liquid or gaseous samples, preferably corresponding alcohols in which R' is an alkyl group having 1–10 carbon atoms, specially preferred 1–5 carbon atoms.

A preferred class of alkanols which can be determined using the inventive sensors are primary alkanols having the formula stated before which accordingly comprise totally 1–5 carbon atoms.

The inventive sensors are specially suited for the determination of ethanol in liquid or gaseous samples, like e.g. alcoholic beverages, liquid or gaseous samples of biologic origin, like urine, blood, blood serum or in corresponding gaseous probes, like e.g. the air which is exhaled by the person which has to be tested.

The keto compounds of formula I, the preferred keto compounds defined before, including the azo keto compounds of formula III are preferably present supported on a carrier material or embedded in a carrier material, preferably a corresponding inert carrier material.

Preferred inert carrier materials are corresponding polymer materials, and as example of preferred carrier materials there are mentioned the following products: cellulose, cellulose derivatives, silicon containing polymer materials like silicon rubber, polymeric materials based on polyesters, polyamides, polyethers as well as homopolymers or copolymers of ethylenically unsaturated monomers. Preferred examples of homopolymers and copolymers of ethylenically unsaturated monomers, are the homopolymers and copolymers of the following monomeric components: styrene, vinylacetate, vinylalcohol, butadiene, ethylene, propylene and halogenated ethylenically unsaturated monomers.

Preferred halogenated ethylenically unsaturated monomeric units of said homopolymers and copolymers are chlorinated or fluorinated ethylenically unsaturated monomeric materials, and preferably the corresponding polymeric materials are homopolymers or copolymers of vinylchloride or vinylidene chloride.

Optionally in the inventive sensors the polymeric materials into which the keto compounds of formula I, for example the azo keto compounds of formula III, are embedded, can contain furthermore a plasticizer, and such plasticizers are usually preferred which have lipophilic properties.

Preferred plasticizers for the corresponding polymeric materials, like for instance, polymeric materials based on polyvinylchloride homopolymers and copolymers, are ether plasticizers and ester plasticizers.

Preferred examples of plasticizers are ethers which have an aliphatic residue comprising a longer chain which is bonded to said ether oxygen atom as well as furthermore an aromatic residue bonded to the ether oxygen atom. An example for such an ether plasticizer is the o-nitrophenyl-octylether.

Examples for ester plasticizers are dicarboxylic acid diesters and tetracarboxylic acid tetraesters, preferably such esters in which the ester forming alcohol is an aliphatic alcohol having a longer chain, for example an alkanol comprising 4–24, preferably 5–12 carbon atoms. As examples for corresponding dicarboxylic acid diesters, there are mentioned the esters of the adipic acid and the sebacic acid, like e.g. the bis(2-ethylhexyl)-ester of the sebacic acid. Furthermore, as examples for tetracarboxylic acid tetraesters there are mentioned such benzophenone tetracarboxylic acid tetraesters and benzhydrol-tetracarboxylic acid tetraesters which are disclosed in the U.S. Pat. Nos. 4,783,496 and 4,857,573 of Simon et al.

It has furthermore been known for a long time that certain components, specially components selected from the group of dicarboxylic acid diamides, have the ability of forming lipophilic complexes with cations and it is furthermore well known in the art that corresponding polymeric materials into which said cation selective component is embedded, can be used for the electrometric determination of the corresponding cations in many fields of application, specially also in the clinical field of application. Usually said polymeric materials contain in addition to the cation selective component furthermore also a plasticizer.

It is furthermore known that in an analogous way also anions can be determined by using as corresponding ion selective component, a component which has a selectivity for the anion in question.

If furthermore the corresponding lipophilic complex forming agent which has a cation selectivity comprises a chromophorous group which results in an alternation of the optical properties of the complex forming agent, when the corresponding complex is formed with the cation in question, then the corresponding membranes are also suited for an optical determination of the cations. The same is also true if in the course of the formation of the complex of the cation and the complex forming agents there is liberated a substance, like e.g. a proton, which can be determined through optical means, like e.g. through a pH-indicator. Analogous performances for an optical determination of anions are as well known in the art.

In as far as the optical determination of anions and cations is concerned, the polymeric material which contains the cation selective, respectively anion selective component, and usually furthermore a plasticizer, advantageously comprises as further component a substance which results in a coextraction of the cation with the corresponding salt forming anion, from the aqueous phase of the aqueous sample into the phase of the polymeric material, respectively a further component which results in an ion exchange through which an anion contained in the polymeric material is exchanged against an anion which is contained in the aqueous sample solution. Typical examples of such further components which are contained in the polymeric material which have the ability to provide an anion exchange of anions contained in the polymeric material against anions contained in the sample solution, are quaternary ammonium salts in which to the nitrogen atom of said quaternary ammonium salt there is bonded at least one lipophilic group, for example an alkyl chain having 4–20 carbon atoms.

It is clearly evident for a person experienced in the art that the alcohols which are to be determined with the inventive sensors, are no substances which have ionic properties. However, nevertheless it was quite unexpectedly found out that it is advantageous to incorporate into the polymeric material of the inventive sensors furthermore a component which enables the ion exchange between ions which are contained in the polymeric material and ions which are contained in the aqueous system of the liquid or gaseous samples in which the alcohol is to be determined.

Preferred examples of corresponding substances which make possible such an ion exchange, are quaternary ammonium salts, specially such quaternary ammonium salts in which there is bonded to the nitrogen atom of said quaternary ammonium salt at least one alkyl group having 4–20 carbon atoms, like e.g. a corresponding straight chain alkyl group. The halides of corresponding quaternary ammonium halides have the ability to perform an ion exchange between the polymeric material and ions which are contained in the liquid or gaseous sample solution. It was found out that the halide anion of the quaternary ammonium salt is exchanged for hydroxy ions of the sample solution if the corresponding polymeric material is brought into contact with the sample solution. It was furthermore found out that through such an ion exchange of halide ions against hydroxy ions, the pH-range within the polymeric material is shifted into the basic or alkaline direction. Such a shifting is advantageous because through a basic environment the reaction of the keto compound of formula I with the alcohol of formula $$R'OH$$

which yields the hemiacetal of formula II is catalyzed.

Because of said reasons a catalyzing of the reaction which yields the hemiacetal and accordingly a fast proceeding of said reaction, is also catalyzed if the corresponding keto compound of formula I which are the starting material for the inventive hemiacetals of formula II, have substituents which show basic properties, and which substituents are bonded to the aromatic residue Ar, or if in said keto compounds of formula I Ar is a heterocyclic radical which has basic properties, like e.g. a corresponding heterocycle which contains a nitrogen atom, like the pyridine nucleus. Because of the reasons outlined above in the polymeric material of the inventive sensors there are advantageously contained further components which result in an ion exchange when the sensor is brought into contact with an aqueous medium, and through which ion exchange the pH-range in the polymeric material is raised in direction to a basic environment. Preferred examples of such components which shift the pH-range in the polymeric material are the quaternary ammonium salts mentioned before.

It is obvious for a person experienced in the art that the inventive hemiacetals of formula II in principle would have the ability to react with a further molecule of the alcohol of formula $$R'OH$$

to yield the corresponding full acetals and that accordingly the OH-group of the inventive hemiacetal of formula II could be substituted by a further residue of formula —OR' yielding the corresponding full acetal, and wherein accordingly in the course of said reaction, one molecule of water is eliminated. It is furthermore evident for a person experienced in the art that it is not advantageous if a corresponding full acetal is formed, because through said reaction with a further molecule of the alcohol to be determined by corresponding sensors, the sensitivity of the determination is lower, respectively in as far as quantitative tests are concerned, the results of such quantitative tests are falsified.

The reaction of the hemiacetal of formula II with a further molecule of the above stated alcohol which yields the full acetal, is catalyzed through a pH-value in the acidic range of pH-values. Because of said reason it is as well advantageous if in the inventive hemiacetals of formula II, respectively in the keto compounds of formula I from which the inventive hemiacetals are formed, there are present substituents which have basic properties or heterocyclic residues which have basic properties or if in corresponding sensors there is present a further component which results in that during the performance of the determination of the alcohol in an aqueous medium, the pH-range is shifted to the alkaline region, respectively if at least the development of an acidic environment is prevented.

It is furthermore well known in the art that the keto compounds of formula I have the ability to form with water hydrates which have a similar structure to the inventive hemiacetals of formula II, i.e. the hydrates in question correspond to the following formula V

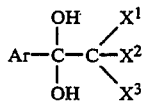

The forming of the hydrates of formula V is a reaction which is catalyzed through basic conditions. It now was quite unexpectedly found out that nevertheless with the inventive sensors alcohols can be tested in aqueous solutions of the corresponding alcohols, and that a quantitative test for the alcohol in question has a good sensitivity. Specially high sensitivities are achieved if in the corresponding sensors the keto compound of formula I is embedded in a polymeric material, preferably one of the polymeric materials mentioned before, like polyvinylchloride.

It it known from the prior art, e.g. from the European patent publication no. 0 281 829 and the corresponding U.S. Pat. No. 5,037,968 of Simon et al. that prior art keto compounds which correspond to the formula A stated before, have the ability to form adducts with oxa acids, for example adducts with carboxylic acids. Because of said adduct formation with the oxa acids it was believed that the inventive sensors which contain as alcohol sensitive component the keto compounds of formula I, would not be usable to determine alcohols in such aqueous systems which furthermore contain organic acids. Quite contrary to this assumption, it was now surprisingly found out that the inventive sensors are suited for a determination of alcohols in such aqueous systems which contain rather high quantities of organic acids, like alcoholic beverages, specially wine.

When the keto compound of formula I which is contained in the inventive sensor reacts with the alcohol to be determined, yielding the new hemiacetal of formula II, then a conjugation of the carbon oxygen double bond of the keto compound with the aromatic system is destroyed, and accordingly a shifting of the light absorption to shorter ranges of wave length, i.e. a hypsochromic shifting occurs when the keto compound of formula I is converted into the new hemiacetal of formula II (see the reasons stated before).

The optical determination of the alcohol content in liquid samples and gaseous samples accordingly is advantageously performed by measuring the absorption at a range of wave length in which the keto compound of formula I has a strong absorption, and by monitoring the fading of said absorption at the stated range of wave length in the course of the formation of the hemiacetal. Tests showed that said method yields results which enable a quantitative determination of the corresponding alcohols and that the corresponding test results furthermore have a good reproducibility.

As already mentioned before, in principle alcohols which correspond to the formula

R'—OH, wherein R' is an aliphtic or cycloaliphtic residue, can be determined with inventive sensors which contain keto compounds of formula I. Preferably, however, the alcohols which are monitored in aqueous samples are alkanols having 1-10 carbon atoms. It furthermore was found out that primary alcohols are preferred in the formation of the hemiacetals over corresponding secondary alcohols and tertiary alcohols.

Preferred alcohol components which are determined with the inventive sensors, respectively preferred alcohol components of the inventive hemiacetals of formula II are accordingly primary alcohols with 1-5 carbon atoms, specially methanol, ethanol, 1-propanol and 1-n-butanol. The tests which were performed showed that the selectivity of the keto compounds of formula I for the mentioned primary alcohols methanol, ethanol, 1-propanol and 1-n-butanol, is very similar. Contrary to it, however, isopropanol and tert.-butanol are discriminated if compared with the above stated primary alcohols by a factor of about 10.

A preferred field of application is the use of the inventive sensors for the determination of ethanol in aqueous systems, for example in alcoholic beverages. In said field of application it is not disadvantageous that the content of ethanol which is determined with the inventive sensors would be falsified through the presence of 1-propanol or 1-n-butanol, because said alcohol components comprising 3, respectively 4 carbon atoms, are absent in corresponding alcoholic beverages or are present in only very low quantities. Contrary to this, however methanol can be present in alcoholic beverages which had been submitted to a destillation process, like brandies, in quantities of up to 1 g per 100 ml of ethanol which is contained in said spirits or brandies. Therefore a falsification of the ethanol content of such alcoholic beverages due to the presence of methanol, is to be expected, if the ethanol determination is performed with the inventive sensors. With regard to this, however, it is to be remarked that also the ethanol determination which is performed according to the enzymatic methods described in the prior art, is falsified through the presence of other primary alcohols, and in some instances even through the presence of secondary alcohols.

Alcoholic beverages, like wines, beers and liquors, can contain rather high quantities of sugar constituents, which sugar constituents comprise monosaccharides and disaccharides as well. In spite of the fact that sugar constituents comprise in their molecule several alcohol groups, nevertheless the inventive sensors are also suited for a quantitative determination of alcohol in such alcoholic beverages which have rather high contents of sugar constituents. When ethanol is determined in an alcoholic beverage which contains rather high quantities of sugar constituents, then a high sensitivity for ethanol is achieved with such sensors in which a keto compound of formula I is embedded in a polymeric material. Corresponding tests which were performed showed that keto compounds of formula I which are embedded in a polymeric material, exclusively react with the above mentioned primary alcohols having 1-5 carbon atoms yielding the inventive hemiacetals, while sugar constituents which are as well present in the test samples, do not react with the keto compounds of formula I, provided that said keto compound is embedded in a polymeric material.

The present invention is now further illustrated through examples.

EXAMPLE 1

Preparation of a membrane for the optical determination of alcohols in aqueous alcoholic solutions Membranes were prepared which contained a keto compound corresponding to formula I embedded in a polymeric material, i.e. in a polyvinylchloride having a high molecular weight.

The corresponding polymer membranes in which the polymeric material was polyvinylchloride contained as further component a plasticizer with lipophilic properties and furthermore a quaternary ammonium chloride in which there was bonded to the nitrogen atom at least one alkyl group having 4–20 carbon atoms, and in which quaternary ammonium chloride there were bonded to the nitrogen atom thereof preferably two or three long chain alkyl groups having 8–16 carbon atoms.

The prepared membranes had the following composition:

| component | parts by weight |
| --- | --- |
| polyvinylchloride | 70–100 |
| plasticizer | 50–80 |
| quaternary ammonium salt | 1.5–4 |
| keto compound corresponding to formula I | 5–10 |

The corresponding membranes for the determination of alcohols by optical means where prepared by dissolving the above stated components, i.e. the polymeric material, the plasticizer, the quaternary ammonium salt and the keto compound of formula I, in an volatile organic solvent, preferably in freshly distilled tetrahydrofuran. The solution thereafter was casted onto plates, for instance plates of quartz glass (fused silica ). The corresponding solution was casted onto the plates of quartz glass in such a quantity that after the solvent had evaporated, there remained a membrane of plastic material having a thickness of 3–5 $\mu$m, preferably a membrane having a thickness of about 4 $\mu$m.

When the samples were tested for alcohols using said membranes, then before the determination of the alcohols in the sample solution the membrane was immersed for some minutes in distilled water for performing the necessary conditioning of the membranes.

EXAMPLE 2

According to the method described in example 1, membranes for the determination of alcohols were prepared, which membranes contained as keto compound which corresponds to formula I a corresponding compound in which the radical Ar is a benzene nucleus which comprises as substituent an acylated amino group which corresponds to the following formula

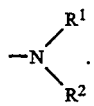

In said formula the radical $R^1$ is the acyl residue of a carboxylic acid and the residue $R^2$ is a hydrogen atom or an alkyl residue and wherein in the acylated amino group having the above stated formula, at least one of the residues $R^1$ or $R^2$ is a long chain alkyl residue, respectively comprises a long chain alkyl radical in a corresponding acyl residue of a long chain alkane carboxylic acid. Preferably the corresponding alkyl residue or acyl residue comprises 8–20 carbon atoms.

The plasticizer which was used in the present examples was a lipophilic plasticizer based on a dicarboxylic acid diester, i.e. the bis(2-ethylhexyl)-ester of the sebacic acid.

As quaternary ammonium salt which has lipophilic properties and which was used as component of the membranes described in the present examples, there was incorporated the methyl-tridodecyl-ammonium-chloride.

The corresponding membranes were prepared according to the procedure described in example 1 and 85 mg of polyvinylchloride, 65 mg of the stated plasticizer, 2.5 mg of the stated quaternary ammonium chloride, as well as 7.8 mg of a keto compound corresponding to formula I, in which the substituent which is bonded to the benzene nucleus, is an acylated amino group in which the substituents $R^1$ and $R^2$ are selected from the substituents mentioned above, were dissolved in 1.5 ml of freshly distilled tetrahydrofurane. Thereafter, the solution was cast onto quartz glass plates yielding membranes which had a thickness of about 4 $\mu$m, when the tetrahydrofurane was evaporated.

EXAMPLE 3

Performance of the determination

The membranes for the determination of the lower alcohols in aqueous solutions were prepared according to the procedure described in the preceding example 1, respectively in the preceding example 2. Said membranes were used in measuring cells which are described in the publication of K. Seiler, W. E. Morf, B. Rusterholz and W. Simon, Anal. Sci., 5 (1989), pages 557 and following. Said determination was performed in cells having two plates of quartz glass on which the corresponding membranes were mounted in the same way as described in the above stated publication. The determination was furthermore performed using a corresponding cell for comparison, and in said cells there were mounted onto the quartz glass plates no corresponding membranes.

The test was performed by inserting the measuring cell and the cell for comparison into a spectrophotometer for the determination of the light absorption in the ultraviolet range and in the visible range of wave length, and the alternation of the spectrum of absorption was determined in the stated wave range according to the method of transmission. The used spectrophotometer was the model 555 of the Perkin Elmer Company, Küsnacht, Switzerland.

Attention was paid that the temperature of the measuring chamber which inserted in said spectrophotometer was maintained at a constant temperature of 25° C. during the performance of the test. This was achieved by using a newly developed bottom part of the measuring cell around which bottom part there circulated water which was brought to the desired temperature using a thermostat.

The calibration was performed by using pure water and furthermore mixtures of water and corresponding alcohols which had different alcohol contents up to a maximum value of 65 vol.-% of alcohol.

The tested alcohols were selected from the group of the following primary alcohols: methanol, ethanol, 1-proponal and 1-butanol, and furthermore also the two following further alcohols were tested: tertiary butanol and isopropanol.

The activity coefficients for water and the above stated alcohols were calculated for the corresponding mixtures, by using for the determination of ethanol the formalism of Margules, and for the determination of the other alkanols selected from the above stated group, the formalism of Van Laar. Said formalisms were used according to the procedures described in the publication of J. Gmehling and U. Onken, in Behrens and R. Eckermann (Eds.), Vapor-Liquid Equilibrium Data Collection, volume 1, publishing and printing company Friedrich Bischoff, Frankfurt, Germany, 1977.

When the corresponding polymeric membranes based on polyvinylchloride which contained as indicator the keto compound of formula I, were brought into contact with an aqueous solution of an alcohol having the formula

R'OH then the corresponding alcohol was extracted from the aqueous phase into the organic phase of the polymeric membrane. In the organic phase of the polymer membrane then the inventive process proceeded, i.e. the keto compound of formula I reacted with the alcohol of the stated formula yielding the new inventive hemiacetal of formula II.

However, as explained before, also water which is contained in the sample solution containing water and the stated alcohol, has the ability of entering from the aqueous phase into the organic phase of the polymeric membrane. The water which enters into the organic phase of the polymer membrane is furthermore able to react in the polymer membrane with the keto compound of formula I to form a corresponding hydrate. Therefore, when the polymeric membrane is brought into contact with the aqueous solution of the alcohol which corresponds to the formula

R'OH then in the polymeric membrane the following equilibria are expected:

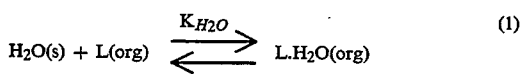

(1)

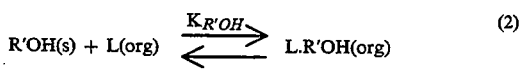

(2)

In the above equations (1) and (2) the used index (s) means solution, i.e. said index refers to the water and the alcohol of formula R'OH respectively, which is present in the aqueous test solution containing alcohol and water.

The term L(org) means the electrically neutral ligand, i.e. the keto compound of formula I, which is present in the organic phase, i.e. in the polymeric membrane.

In the reaction illustrated with the equilibrium (1) above, furthermore the term L.H₂O(org) means the water which was introduced into the membrane through an extraction reaction, and which water furthermore reacted in the membrane with the keto compound of formula I converting said keto compound into the corresponding hydrate.

In the equilibrium which is illustrated through the reaction (2) in an analogous way the term L.R'OH(org) means the alcohol R'OH which is extracted into the polymer membrane and is converted in the polymer membrane into the new hemiacetal of formula II through the reaction with the keto compound of formula I which is contained in said polymeric membrane.

It depends from the corresponding equilibrium constant $K_{H_2O}$ and the equilibrium constant $K_{R'OH}$ respectively to what extent the equilibrium reaction illustrated by formula (1) and formula (2) is shifted from the left side to the right side when the corresponding polymeric membrane is brought into contact with an aqueous solution which contains water as well as an alcohol of formula R'OH.

The corresponding equilibrium constant $K_{H_2O}$ and $K_{R'OH}$ respectively depends from the respective complex formation constant for the formation of the hydrate, and for the formation of the hemiacetal, and said equilibrium constant further also depends from the distribution coefficient of the water on one hand and the alcohol having the stated formula on the other hand, between the aqueous phase of the sample solution (s) and the organic phase of the polymeric membrane (org).

When furthermore the polymeric membrane is brought into contact with the solution containing water and the alcohol as well, then there is assumed that in the organic phase of the membrane there is only formed the corresponding hydrate of the keto compound of formula I, and furthermore only the hemiacetal of formula II of the keto compounds of formula I and the corresponding alcohol which is contained in the aqueous solution, and that accordingly no full acetal is formed. The corresponding hemiacetal is the reaction product when one mol of the alcohol reacts with one mol of the keto compound of formula I.

It is furthermore assumed that the distribution coefficient between the aqueous phase of the sample solution and between the organic phase of the polymeric membrane is constant for water and for the corresponding alcohol if the organic membrane comes into contact with the aqueous sample solutions having an alcohol content of up to 65% by volume. Since, furthermore, the membrane matrix is not changed dramatically in its composition when the keto compound of formula I reacts with the alcohol and the water respectively, the activity of H₂O and R'OH in the membrane can be replaced by the concentration of said compounds.

Therefore the selectivity coefficient of the optode membrane for the corresponding alcohol compared with the corresponding selectivity coefficient for water, is given through the ratio of the equilibrium constant of the two specia drawn into consideration.

The selectivity coefficient $$K^{opt}_{R'OH,H_2O}$$

of the optode membrane for water over the corresponding alcohol of formula R'OH which has to be determined in the aqueous solution of said alcohol in water, accordingly is given by the following equation (3)

$$K^{opt}_{R'OH,H_2O} = K_{H_2O}/K_{R'OH} \qquad (3).$$

From said equation (3) there can be also seen that a corresponding optode membrane has a good selectivity coefficient for the alcohol to be determined over water, if said selectivity coefficient $$K^{opt}_{R'OH,H_2O}$$

has a value which is small, i.e. which is far below 1.

EXAMPLE 4

According to the process described in example 2 there was prepared an optode membrane. Said membrane contained as keto compound of formula I a compound corresponding to the following formula

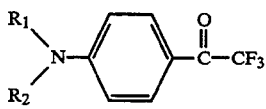

In said formula
$R_1$ was the acetyl residue of formula

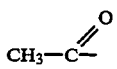

and the residue
$R_2$ the n-dodecyl residue.

For said membrane the equilibrium constants were determined for different systems containing water and the corresponding alcohol, and the corresponding selectivity coefficients were calculated according to the procedure explained in example 3.

In the following table 1 the logarithm of the equilibrium constant K is given for substrates i which are water, respectively the alcohols stated in the following table 1. Reference is made to the equations (1) and (2) which are explained in the preceding example 3.

Furthermore, in table (1) the logarithm of the selectivity coeffient of the corresponding optode membrane for ethanol, which is abbreviated as EtOH over water, respectively over the alcohols stated in said table, is given, i.e. the value $$\log K^{opt}_{EtOH,i}$$

With regard to this we refer to column 3 of the following table.

TABLE 1

| Substrate i | log $K_i$ | log $K^{opt}_{EtOH,i}$ |
|---|---|---|
| water | 0.2 | −1.1 |
| ethanol (EtOH) | 1.3 | 0 |
| methanol | 1.5 | +0.2 |
| 1-propanol | 1.2 | −0.1 |
| 1-butanol | 1.5 | +0.2 |
| tert.-butanol | 0.2 | −1.1 |
| isopropanol | 0.4 | −0.9 |

There can be seen from the results which are summarized in the above stated table 1 that the corresponding optode membranes have a high selectivity for the alcohols methanol, ethanol, 1-propanol and 1-butanol over water, and that said optode membranes furthermore have a high selectivity for each of the alcohols selected from the above stated group over the alcohols tert.-butanol and isopropanol.

The corresponding optode membranes accordingly are well suited for an optical determination of the above stated primary alcohols in corresponding samples which contain said primary alcohols mixed with water.

There can be furthermore seen from the above stated table that the corresponding membranes even have a slightly higher selectivity coefficient for methanol over water than for ethanol over water.

The specific keto compound of formula I which was tested in the present optode membranes as optical indicator, has a maximum of absorption at 305 nm, while the corresponding new inventive hemiacetals of formula II which are formed with said keto compounds of formula I and the alcohols stated in table (1) as well as the corresponding hydrate of the keto compounds of formula I have a maximum of absorption which is below 210 nm.

Corresponding tests showed that if said optode membrane is brought into contact with an aqueous solution of a phosphate buffer which has a pH-value of 7, then the maximum of absorption at 305 nm remains unchanged.

If, however, said optode membrane is brought into contact with a solution of said phosphate buffer which furthermore contains one of the primary alcohols selected from the group consisting of methanol, ethanol, 1-propanol and 1-butanol, and if in said test solution the concentrations of the alcohols are increased, for instance in a range of 1 vol.-% of the corresponding alcohol up to 33 vol.-% of the corresponding alcohol, then the maximum of absorption at 305 nm by-and-by gets weaker, proportional to the increase of the concentration of alcohol in the tested alcoholic sample solution.

If furthermore in a diagram the relative absorption at 305 nm is plotted at the ordinate and the logarithm of the concentration of ethanol is plotted at the abscissa, then the corresponding values of the curve of the corresponding plotted values are lying on a part of said curve which is nearly linear in the range of 1 vol.-% of ethanol to 32 vol.-% of ethanol. Therefore, the corresponding sensors, i.e. the optode membranes are perfectly suited for the determination of ethanol in alcoholic beverages.

EXAMPLE 5

Determination of the alcohol content of alcohol free wine, different kinds of white wines, red wines and rosé wines, as well as different kinds of beers and spirits, respectively brandies, using the optode membranes described in example 4

The determination of the alcohol content was performed according to the transmission method described in example 3 at a wave length of 305 nm, using the apparatus described in example 3. The alcoholic beverages optionally have a rather extensive absorbance in the above stated range of wave length, due to the coloration of said beverages. Because of this, in each of the tests portions of 50 ml of the alcoholic beverage or non alcoholic beverage to be tested were mixed with 1 g of activated charcoal and thereafter said samples were filtered. The used activated charcoal was the product designated as Purissimum p.a. of the Fluka Company, Buchs, Switzerland.

After said filtration procedure all the samples to be tested were diluted with a phosphate buffer having a pH-value of 7 in a volume ratio of 1:1. In as far as spirits or brandies are concerned, however before the addition of said buffer, said beverages of high alcohol content were diluted with distilled water in a volume ratio of 2:3. Said dilution step was performed in order to bring the alcohol content of said highly alcoholic beverages into a range which is similar to that of wine.

In the following table 2 in column 2 thereof having the title "optode membrane" are given the corresponding values which were obtained with the inventive sensors, i.e. the optode membranes. After each value there is stated the standard deviation (the value after the symbols ±) of three determinations performed with three samples of the same alcoholic beverage.

In the third column of said table which has the title "density method" the corresponding alcohol contents of the tested samples were determined with the distillation method, according to the prior art. In this case the alcoholic beverages were submitted to a distillation and the density of the recovered distilled product was determined. It is stated in the prior art that the standard deviation of said density method is ±0.1% (vol.-% per volume).

The alcohol concentrations are stated in the following table 2 in vol.-%, and also the standard deviations of the determination with the optode membrane are given in vol.-%.

TABLE 2

| sample | optode membrane | density method |
|---|---|---|
| alcohol free wine | 0.71 ± 0.33 | 0.74 |
| beer | | |
| 1 | 4.95 ± 0.10 | 4.89 |
| 2 | 4.62 ± 0.16 | 4.8 |
| 3 | 5.33 ± 0.14 | 5.4 |
| white wine | | |
| 1 | 10.38 ± 0.10 | 10.3 |
| 2 | 10.76 ± 0.07 | 10.9 |
| 3 | 12.05 ± 0.18 | 12.0 |
| red wine | | |
| 1 | 12.33 ± 0.04 | 12.4 |
| 2 | 12.90 ± 0.08 | 12.9 |
| 3 | 11.49 ± 0.10 | 11.9 |
| rosé wine | | |
| 1 | 10.58 ± 0.20 | 11.1 |
| 2 | 10.35 ± 0.11 | 10.9 |
| spirits and brandies | | |
| 1 | 39.06 ± 0.56 | 39.9 |
| 2 | 39.82 ± 0.19 | 39.8 |
| 3 | 39.84 ± 0.29 | 40.2 |

There can be seen from said table 2 that the corresponding values which were obtained with the optode membrane from the tested alcoholic and not alcoholic beverages, are in good agreement with the corresponding values which were determined according to the prior with the distillation-density-method. Also the standard deviation of the determinations performed with the optode membranes were only slightly higher than the standard deviation which is stated in the prior art for the distillation-density-procedure.

As however the determination according to the present invention using optical means is far easier to be performed and far less time-consuming, it is clearly evident that the inventive process is very advantageous.

The corresponding membranes were also used for the determination of the alcohol content of liqueurs. In this case, however, the high sugar content of said liqueurs resulted in that the corresponding values differed somewhat from the values which were determined with the distillation density method. The values which were determined with the optode membranes showed a falsification of the determined values into the direction of higher alcohol contents. Usually the liqueurs had alcohol contents in the range of 20-30 vol.-%, and the alcohol contents determined with the optode membranes were 1 vol.-% to 2 vol.-% higher than the corresponding values which were determined with the distillation-density-method. Said falsification of the test results, however, is not surprising if the extremely high content of sugar constituents of said liqueurs if drawn into consideration.

What I claim is:

1. A process for determining the alcohol content of a liquid or gaseous alcoholic beverage sample containing an alcohol of the formula R'—OH comprising:

A) determining, in the absence of said alcohol, a light absorption or fluorescence of an optical sensor in the ultraviolet, visible or infrared range, the optical sensor comprising a keto compound of formula I

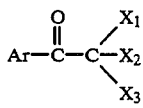

incorporated into or supported by a carrier material;

B) contacting the sample with said optical sensor to form a hemiacetal of formula II

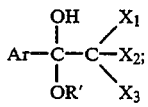

C) determining a change in the light absorption or fluorescence of the optical sensor; and D) determining the alcohol content of the sample based on the change in the light absorption or fluorescence of the optical sensor, wherein R' is an aliphatic or cycloaliphatic residue, $X_1$, $X_2$, and $X_3$ are independently chlorine or fluorine, and Ar is a member selected from the group consisting of:

(a) an aromatic system selected from the group consisting of: substituted benzene, naphthalene, substituted naphthalene, phenanthrene, substituted phenanthrene, anthracene, and substituted anthracene, wherein the substituted molecules have at least one non-acidic substituent selected from the group consisting of nonpolar substituents, weakly polar substituents, basic substituents, and chromophorous substituents; and b) a heterocyclic system selected from the group consisting of: thiophene, substituted thiophene, furan, substituted furan, benzofuran, substituted benzofuran, benzothiophene, substituted benzothiophene, pyrrole, substituted pyrrole, 1,2-diazole, substituted 1,2-diazole, 1,3-diazole, substituted 1,3-diazole, triazole, substituted triazole, pyridine, substituted pyridine, thiazole, substituted thiazole, 1,2-diazine, substituted 1,2-diazine, 1,3-diazine, substituted 1,3-diazine, 1,4-diazine, substituted 1,4-diazine, 1,3,5-triazine, substituted 1,3,5-triazine, 1,2,4-triazine, substituted 1,2,4-triazine, 1,2,3-triazine, substituted 1,2,3-triazine, tetrazine, substituted tetrazine, 1-azanaphthalene, substituted 1-azanaphthalene, 2-azanaphthalene, substituted 2-azanaphthalene, diazanaphthalenes, substituted diazanaphthalenes, triazanaphthalenes, substituted triazanaphthalenes, indole, substituted indole, carbazole, substituted carbazole, monoazaanthracenes, substituted monoazaanthracenes, diazaanthracenes, substituted diazaanthracenes, triazaanthracenes, substituted triazaanthracenes, triazaphenanthrenes, substituted triazaphenanthrenes, tetraazaanthracenes, substituted tetraazaanthracenes, tetraazaphenanthrenes, and substituted tetraazaphenanthrenes, wherein the substituted molecules have at least one non-acidic substituent as defined in a) above.

2. The process of claim 1, wherein the chromophorous substituent of the aromatic or heterocyclic system has the ability to fluoresce and through the formation of the hemiacetal of formula II from the keto compound of formula I fluorescence is created or quenched.

3. The process of claim 1, wherein R' is an alkyl group having 1–10 carbon atoms.

4. The process of claim 1, wherein R' is an alkyl group of the formula $R^3$—$CH_2$— wherein $R^3$ is hydrogen or an alkyl group having 1–4 carbon atoms.

5. The process of claim 1, wherein

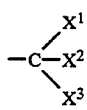

in the keto compound of formula I is a trifluoromethyl group.

6. The process of claim 1, wherein the substituents are selected from the group consisting of: halogen, nitro, unsubstituted alkyl, substituted alkyl, unsubstituted alkenyl comprising one or more carbon-double bonds, substituted alkenyl comprising one or more carbon-carbon-double bonds, unsubstituted alkynyl, substituted alkynyl, unsubstituted cycloalkyl, substituted cycloalkyl, unsubstituted aryl, substituted aryl, unsubstituted heterocyclic, and substituted heterocyclic.

7. The process of claim 6 wherein

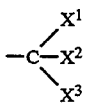

in the keto compound of formula I is a trifluoromethyl group.

8. The process of claim 1, wherein the substituents are selected from the group consisting of:
ether, —S—$R^{1'}$, —SO—$R^{1''}$, —$SO_2$—$R^{1'''}$, nitrilo, carboxylic acid ester, carboxylic acid amide, sulfonamide, hydroxy, esterified hydroxy, and
wherein the radicals $R^1$, $R^{1'}$, $R^{1''}$, or $R^{1'''}$ are independently selected from the group consisting of hydrogen, unsubstituted alkyl, substituted alkyl, unsubstituted alkenyl substituted alkenyl, unsubstituted alkynyl, substituted alkynyl, unsubstituted cycloalkyl, substituted cycloalkyl, unsubstituted aryl, substituted aryl, unsubstituted heterocyclic, and substituted heterocyclic, and the radical $R^2$ is selected from the group consisting of

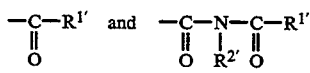

wherein $R^{1'}$ and $R^{2'}$ have the same meaning as stated above for $R^1$.

9. The process of claim 8 wherein

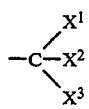

in the keto compound of formula I is a trifluoromethyl group.

10. The process of claim 1, wherein the substituents are selected from the group consisting of:
primary, secondary, or tertiary amino groups corresponding to the formula

wherein the radicals $R^3$ and $R^4$ are independently from each other selected from the group consisting of hydrogen, unsubstituted alkyl, substituted alkyl, unsubstituted alkenyl, substituted alkenyl, unsubstituted alkynyl, substituted alkynyl, unsubstituted cycloalkyl, substituted cycloalkyl, unsubstituted aryl, substituted aryl, unsubstituted heterocyclic, and substituted heterocyclic, or $R^3$ and $R^4$ form, together with the nitrogen atom to which they are bonded, a heterocyclic residue which can optionally contain in its ring structure in addition to said nitrogen atom, one or more further hetero atoms which are selected from the group consisting of oxygen, sulfur and nitrogen, and which heterocyclic radical is unsubstituted or is substituted with a non-acidic substituent selected from the group consisting of non-polar substituents, weakly polar substituents, basic substituents and chromophorous substituents.

11. The process of claim 10 wherein

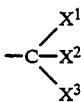

in the keto compound of formula I is a trifluoromethyl group.

12. The process of claim 1, wherein the chromophorous substituent is a group of the formula Ar'—N≡N— wherein Ar' is a member selected from the group consisting of:
(a) an aromatic system selected from the group consisting of: benzene, substituted benzene, naphthalene, substituted naphthalene, phenanthrene, substituted phenanthrene, anthracene, and substituted anthracene, wherein the substituted molecules have at least one non-acidic substituent selected from the group consisting of nonpolar substituents, weakly polar substituents, basic substituents, and chromophorous substituents; and
b) a heterocyclic system selected from the group consisting of: thiophene, substituted thiophene, furan, substituted furan, benzofuran, substituted benzofuran, benzothiophene, substituted benzothiophene, pyrrole, substituted pyrrole, 1,2-diazole, substituted 1,2-diazole, 1,3-diazole, substituted 1,3-diazole, triazole, substituted triazole, pyridine, substituted pyridine, thiazole, substituted thiazole, 1,2-diazine, substituted 1,2-diazine, 1,3-diazine, substituted 1,3-diazine, 1,4-diazine, substituted 1,4-diazine, 1,3,5-triazine, substituted 1,3,5-triazine, 1,2,4-triazine, substituted 1,2,4-triazine, 1,2,3-triazine, substituted 1,2,3-triazine, tetrazine, substituted tetrazine, 1-azanaphthalene, substituted 1-azanaphthalene, 2-azanaphthalene, substituted 2-azanaphthalene, diazanaphthalenes, substituted diazanaphthalenes, triazanaphthalenes, substituted triazanaphthalenes, indole, substituted indole, carbazole, substituted carbazole, monoazaanthracenes, substituted monoazaanthracenes, diazaanthracenes, substituted diazaanthracenes, triazaanthracenes, substituted triazaanthracenes, triazaphenanthrenes, substituted triazaphenanthrenes, tetraazaanthracenes, substituted tetraazaanthracenes, tetraazaphenanthrenes, and substituted tetraazaphenanthrenes, wherein the substituted molecules have at least one non-acidic substituent as defined in a) above.

13. The process of claim 1, wherein the carrier material comprises a polymeric material which is selected from the group consisting of
(i) cellulose,
(ii) cellulose derivatives,
(iii) silicone-containing polymeric materials,
(iv) polyesters,
(v) polyamides,
(vi) polyethers,
(vii) homopolymers and copolymers of ethylenically unsaturated monomers, selected from the group consisting of styrene, vinylacetate, vinylalcohol, butadiene, ethylene and propylene, and
(viii) homopolymers and copolymers of said ethylenically unsaturated monomers, which monomers are halogenated.

14. The process of claim 13 wherein the polymeric material is a homopolymer or copolymer of a chlorinated or fluorinated ethylenically unsaturated monomer.

15. The process of claim 14 wherein the polymeric material is a homopolymer or copolymer of vinylchloride or vinylidene chloride.

16. The process of claim 13 wherein the polymeric material further comprises a plasticizer.

17. The process of claim 16 wherein the plasticizer which present in the polymer component is a lipophilic plasticizer selected from the group consisting of ethers, dicarboxylic acid diesters and tetracarboxylic acid tetraesters, in which diesters and tetraesters the alcohol moiety is an alkanol group comprising 4–20 carbon atoms.

18. The process of claim 10 wherein the polymeric material further contains a quaternary ammonium salt in which there is bonded to the nitrogen atom thereof at least one alkyl group which comprises 4–20 carbon atoms.

19. The process of claim 10 wherein the polymeric material is present in said carrier material in a greater amount by weight than said plasticizer.

20. The process of claim 13 wherein the polymeric material further contains a quaternary ammonium salt in which there is bonded to the nitrogen atom thereof at least one alkyl group which comprises 4–20 carbon atoms.

21. The process of claim 1, wherein the process is performed at a constant temperature.

* * * * *

UNITED STATES PATENT AND TRADEMARK OFFICE
CERTIFICATE OF CORRECTION

PATENT NO. : 5,374,562
DATED : December 20, 1994
INVENTOR(S) : Wilhelm Simon

It is certified that error appears in the above-indentified patent and that said Letters Patent is hereby corrected as shown below:

In The Claims:

Claim 8, Col. 25, line 51, insert the following formula after "and":

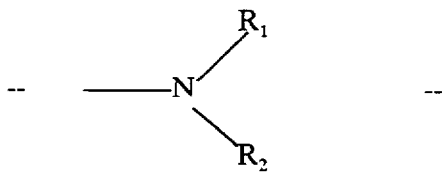

Claim 17, Col. 28, line 16, insert --is-- after "which".

Claim 18, Col. 28, line 22, delete "10" and substitute --16-- therefor.

Claim 19, Col. 28, line 27, delete "10" and substitute --16-- therefor.

Signed and Sealed this

Thirtieth Day of May, 1995

BRUCE LEHMAN

*Attest:*

*Attesting Officer*  *Commissioner of Patents and Trademarks*